United States Patent [19]

Lewis et al.

[11] 4,439,624

[45] Mar. 27, 1984

[54] CONVERSION OF DIMETHYL ETHER TO FORMALDEHYDE USING BI-MO-CU CATALYST

[75] Inventors: Robert M. Lewis, Sugarland; Robert C. Ryan, Houston; Lynn H. Slaugh, Cypress, all of Tex.

[73] Assignee: Shell Oil Company, Houston, Tex.

[21] Appl. No.: 433,320

[22] Filed: Oct. 7, 1982

[51] Int. Cl.$^3$ ............................................. C07C 45/32
[52] U.S. Cl. ..................... 568/470; 568/471; 568/474; 568/479
[58] Field of Search ................ 568/470, 471, 474, 479

[56] References Cited

U.S. PATENT DOCUMENTS

| | | | |
|---|---|---|---|
| 2,075,100 | 3/1937 | Dreyfus | 568/470 |
| 2,246,569 | 6/1941 | Brown | 568/470 |
| 2,467,223 | 4/1949 | Payne | 568/470 |
| 3,655,771 | 4/1972 | Tadenuma et al. | 568/470 |
| 4,024,074 | 5/1977 | Cairati et al. | 568/470 |
| 4,208,353 | 6/1980 | Webster et al. | 568/473 |
| 4,258,216 | 3/1980 | Trecek et al. | 568/473 |
| 4,306,089 | 12/1981 | Webster et al. | 568/473 |

FOREIGN PATENT DOCUMENTS

| | | | |
|---|---|---|---|
| 1239285 | 4/1967 | Fed. Rep. of Germany | 568/474 |
| 1254359 | 11/1967 | Fed. Rep. of Germany | 568/470 |
| 40-23645 | 10/1965 | Japan | 568/474 |
| 56-15601 | 4/1971 | Japan | 568/470 |
| 1065251 | 4/1967 | United Kingdom | 568/470 |
| 413139 | 7/1974 | U.S.S.R. | 568/470 |
| 294465 | 11/1977 | U.S.S.R. | 568/470 |
| 662544 | 5/1979 | U.S.S.R. | 568/472 |

*Primary Examiner*—Werren B. Lone

[57] ABSTRACT

A process is disclosed for oxidizing dimethyl ether to formaldehyde using a catlyst comprising a mixture of oxides of bismuth, molybdenum and copper.

4 Claims, No Drawings

CONVERSION OF DIMETHYL ETHER TO FORMALDEHYDE USING BI-MO-CU CATALYST

FIELD OF THE INVENTION

This invention relates to a process for converting dimethyl ether to formaldehyde utilizing a catalyst which comprises a mixture of oxides of bismuth, molybdenum and copper.

BACKGROUND OF THE INVENTION

Formaldehyde is a chemical used extensively as a reagent, preservative, embalming agent, antiseptic and deodorant, and, industrially, in large quanitities in the synthesis of many substances such as plastics. A process that would convert a readily available syngas chemical such as dimethyl ether to a more valuable substance like formaldehyde would be of commercial interest. A known commercial catalyst for converting dimethyl ether to formaldehyde is tungstic acid (Tadenuma et al, U.S. Pat. No. 3,655,771, issued Apr. 11, 1972). The use of a Mo-Bi-P-Si catalyst is disclosed in Mitsushima, "Synthesis of Formaldehyde by Catalyst Oxidation of Dimethyl Ether", Kogyo Kagaku Zasshi, Vol. 71, No. 3, (1968), pp. 378-382. The use of phosphorus in catalysts for the conversion of dimethyl ether to formaldehyde presents problems of leachability of the phosphorus by water in the system.

SUMMARY OF THE INVENTION

The instant invention comprises the process for oxidizing dimethyl ether to formaldehyde by contacting dimethyl ether and oxygen with a catalyst which comprises a mixture of oxides of bismuth, molybdenum and copper. The catalyst typically contains from about 20 to about 80% by weight of bismuth, measured as the metal, from about 10 to about 50% by weight of molybdenum, measured as the metal, and from about 0.1 to about 10% by weight of copper, measured as the metal. These catalysts are quite stable, have a long life, and are resistant to leaching by the product and by-product make.

DESCRIPTION OF THE PREFERRED EMBODIMENTS

The catalyst utilized in the process of the instant invention comprises an intimate mixture of oxides of bismuth, molybdenum, and copper. The exact form of the oxides in the final catalyst is not known, but it is believed to be a mixture of individual oxides, binary oxides and tertiary oxides. The catalysts are prepared from the oxides per se, from mixtures of the metals which are subsequently oxidized, or from metallic compounds, which upon calcination are converted to the oxides. In general, the catalysts can be prepared in the bulk form, or supported on an inert support.

A preferred method of preparation of the catalysts in the bulk form is by co-precipitation. The three metallic components can be coprecipitated simultaneously, the resultant precipitate washed, filtered, and dried and subsequently calcined in air at a temperature ranging from about 300° C. to about 900° C.

Alternatively, the individual metal components can be precipitated separately and then blended together with high shear mixing apparatus. Another option would be to form a hydrogel of one or more of the metallic components, and then mix in the remaining component(s), and adding a precipitating agent for this other component(s). Other techniques for preparing mixed gels or precipitates would be apparent to one skilled in the art. These precipitates would then be calcined at temperatures ranging from about 300° C. to about 900° C. to convert the gels or precipitates to the oxide forms. Another way of preparing the catalysts would be to spray dry a solution containing salts of the three metallic components and subsequently calcining this spray-dried material. Flame spraying of a solution of the three metallic compounds into an oxidizing atmosphere would be yet again an alternative way of preparing the catalyst.

While in general the catalytic material is preferably utilized in the bulk form, it may be supported on a suitable inert support such as, for example, alumina, silica, magnesia, Kieselguhr, pumice and the like. Preparation of a supported catalyst is also prepared in a typical fashion. For example, by impregnating the inert support with suitable solutions of salts, which decompose upon calcination to the oxides, drying and subsequently calcining in air at about 300°-900° C. to convert the salts to the oxide.

In general, the catalysts will contain as catalytic material, from about 20 to about 80%, preferably from about 30 to about 70% by weight, measured as the metal, of bismuth; from about 10 to about 50%, preferably from about 15 to about 40% by weight, measured as the metal, of molybdenum; and from about 0.1 to about 10%, preferably from about 0.5 to about 6% by weight, measured as the metal, of copper. It is understood that the above cited measurements refer to the catalytic materials, i.e., the oxides (but measured as the metal), and the weight of the support is excluded from these measurements. In general, when a catalyst is utilized in supported form, about 1 to about 30% by weight of the total catalyst will comprise the mixture of catalytic oxides.

In the instant process, formaldehyde is prepared by oxidizing in the vapor phase, dimethyl ether with oxygen. Generally, the oxygen is provided diluted with an inert gas, such as nitrogen. Air provides a suitable oxygen-containing feed gas. Suitable precautions should be taken to avoid hazards of explosive oxygen-hydrocarbon mixtures.

The catalysts utilized in the instant process are used in a fashion typical of that utilized for heterogeneous catalysts. They may be used in fixed beds, or in fluidized beds. Typical reaction temperatures range from about 300° C. to about 600° C. Typical reaction pressures range from about atmospheric to about 500 bars, preferably from about atmospheric to about 200 bars. Typical feed rates include gaseous hourly space velocities ranging from about 500 to about 25,000 l/l/hr.

The process of the instant invention and a preparation of the typical catalyst will be further described below by the following illustrative embodiments which are provided for illustration and are not to be construed as limiting the invention.

ILLUSTRATIVE EMBODIMENTS

The following illustrates the preparation of a catalyst useful in the instant process.

A solution of bismuth trinitrate pentahydrate (48.5 g) and copper dinitrate 2.5 hydrate (3.95 g) in water (100 ml) was added simultaneously with a solution of 12% ammonium hydroxide (75 ml) to a solution of ammonium dimolybdate (34.0 g) in water (100 ml) over a twenty minute period. The mixture was stirred for a two day period, filtered and the solid dried at 120° C. and finally calcined at 500° C. The catalyst was ground and sieved to 10-20 mesh particle size. The resultant catalyst contained about 54%wt Bi, 3%wt Cu and 25%wt Mo.

The following illustrates the use of the catalyst as prepared above in converting dimethyl ether to formaldehyde. For comparison purposes, a catalyst containing only molybdenum and bismuth, prepared in a fashion similar to that above was tested and is given in the accompanying tables as Examples A and B.

The particles were loaded into a quartz tube and were tested in a flow reactor isolated in a barricade cell. The reactor was operated at atmospheric pressure with a volume concentration of dimethyl ether in air of about 4.5-5.6%. The results were a series of runs in which the reactor temperature and catalyst volume (hence, gaseous hourly space velocity) were varied and are tabulated in Table 1.

We claim:

1. A process for converting dimethyl ether to formaldehyde which comprises contacting the dimethyl ether with oxygen at a temperature ranging from about 300° C. to about 600° C. with a catalyst comprising a mixture of oxides of bismuth, molybdenum and copper wherein the catalyst contains about 20 to about 80% by weight of bismuth, measured as a metal, from about 10 to about 50% by weight of molybdenum measured as the metal and from about 0.1 to about 10% by weight of copper, measured as a metal, exclusive of any inert support.

2. The process of claim 1 wherein the bismuth ranges from about 30 to about 70%, the molybdenum ranges from about 15 to about 40% and the copper ranges from about 0.5 to about 6%.

3. The process of claim 1 wherein the pressure ranges from about atmospheric to about 500 bar.

4. The process of claim 1 where the gaseous hourly space velocity ranges from about 500 to about 25,000 l/l/hr.

TABLE 1

| Ex. | Catalyst | Temp. °C. | GHSV | Conv. % | Selectivity % $H_2CO$ | CO | $CO_2$ | $H_2CO$ Yield % |
|---|---|---|---|---|---|---|---|---|
| 1 | 54% Bi—25% Mo—3% Cu | 400 | 8000 | 34 | 41 | 38 | 21 | 14 |
| 2 | 54% Bi—25% Mo—3% Cu | 450 | 8000 | 36 | 43 | 38 | 18 | 16 |
| 3 | 54% Bi—25% Mo—3% Cu | 500 | 5300 | 34 | 44 | 39 | 16 | 15 |
| 4 | 54% Bi—25% Mo—3% Cu | 500 | 4000 | 39 | 43 | 39 | 16 | 17 |
| 5 | 54% Bi—25% Mo—3% Cu | 400 | 4000 | 40 | 36 | 35 | 29 | 14 |
| 6 | 54% Bi—25% Mo—3% Cu | 500 | 2000 | 40 | 39 | 34 | 27 | 16 |
| A | 55% Bi—25% Mo | 500 | 16000 | 32 | 28 | 50 | 21 | 9 |
| B | 55% Bi—25% Mo | 500 | 8000 | 24 | 14 | 58 | 28 | 3 |

* * * * *